United States Patent
Brem et al.

(10) Patent No.: US 7,368,235 B2
(45) Date of Patent: May 6, 2008

(54) METHOD FOR IDENTIFYING READING FRAME MUTATIONS

(75) Inventors: Gottfried Brem, Hilgertshausen (DE); Thomas Czerny, Wien (AT)

(73) Assignee: Apogene Biotechnologie GmbH & Co. KG, Hilgertshausen (DE)

( * ) Notice: Subject to any disclaimer, the term of this patent is extended or adjusted under 35 U.S.C. 154(b) by 460 days.

(21) Appl. No.: 10/483,277

(22) PCT Filed: Jul. 10, 2002

(86) PCT No.: PCT/EP02/07701

§ 371 (c)(1),
(2), (4) Date: Jul. 6, 2004

(87) PCT Pub. No.: WO03/010334

PCT Pub. Date: Feb. 6, 2003

(65) Prior Publication Data

US 2004/0234987 A1     Nov. 25, 2004

(30) Foreign Application Priority Data

Jul. 10, 2001    (EP)  ................... 01116865

(51) Int. Cl.
*C12Q 1/68*     (2006.01)
(52) U.S. Cl. ........................................ 435/6; 435/91.41
(58) Field of Classification Search .................... None
See application file for complete search history.

(56) References Cited

U.S. PATENT DOCUMENTS 5,876,940 A     3/1999   Groden et al.

FOREIGN PATENT DOCUMENTS

EP     0 872 560     10/1998
JP     62186786     8/1987

OTHER PUBLICATIONS

Magliery et al., Eur. J. Biochem. vol. 271 (2004), pp. 1595-1608.*
LiMuti et al. (1989) "Colorimetric detection of microbially excreted lysine directly on agar plates," J. Micro. Meth. 9:129-137.

* cited by examiner

*Primary Examiner*—James S Ketter
(74) *Attorney, Agent, or Firm*—Knobbe, Martens Olson & Bear LLP

(57) ABSTRACT

The invention relates to a simple and rapid method for identifying mutations in a gene of interest indicating an alteration in the reading frame of the proteins derived therefrom. The inventive method more particularly relates to the use of said method for scanning the animal population.

10 Claims, 3 Drawing Sheets

METHOD FOR IDENTIFYING READING FRAME MUTATIONS

RELATED APPLICATIONS

This application represents the U.S. National Phase of International Application No. PCT/EP02/07701 filed Jul. 10, 2002, designating the United States of America and published in German, which claims the benefit of priority of European Patent application No. 01116865.5 filed Jul. 10, 2001.

FIELD OF THE INVENTION

The present invention relates to a simple and quick process for identifying in a gene of interest mutations which result in a change to the protein derived therefrom. The present invention relates in particular to the use of this process in the screening of populations to isolate mutants and for the early detection of an individual's predisposition to develop diseases.

BACKGROUND OF THE INVENTION

The basis for each evolutionary development is a natural mutation rate via which the genome experiences spontaneous changes. Although the majority of these mutations do not in any way affect essential functions, a certain percentage can nevertheless have serious consequences, such as the occurrence of or predisposition to develop diseases which are passed on to the offspring (hereditary diseases). If such mutations are recessive, this does not result in any disadvantages to the individual affected as the allele or its product will still fulfil its biological role. In each new generation of a population, therefore, recessive mutations occur generally without any far-reaching change to the phenotype. Only where there is interbreeding with a second heterozygotic individual with a mutation in the same gene, are negative effects on the offspring to be expected.

Induced mutations, caused for example by the targeted use of chemicals and/or radiation, have proved extremely helpful in the genetic analysis of biological and also medical problems. If one parent is exposed to mutagenic reagents, the following F1 generation includes heterozygotic offspring who are mutation carriers, but usually do not have a changed phenotype. Only a complicated interbreeding pattern continuing into the F3 generation allows the phenotypes of these recessive mutations to be evident in homozygotic individuals. In view of the complex and time-consuming state-of-the-art processes to determine mutations of this kind, there is a need for a simpler process.

A process for detecting nonsense mutations has already been described in EP 0 872 560 whereby by means of homologous recombination a construct is produced which contains the gene to be tested downstream of a promoter and, in the same reading frame with the gene to be tested, contains a so-called reporter gene. At the expression of the reading frame, a fusion protein is formed which contains the reporter gene function. This can be detected via phenotype properties, such as resistance to antibiotics, enzymes which can be detected by appropriate processes or the ability of cells containing the construct to grow on certain culture mediums.

A disadvantage of this process however is that in an initial stage, screening must be carried out on the successful recombination of the gene fragment to be tested with the vector. Only in a second stage can the presence of the reporter function then be proven. A further problem with this process lies in the detection of heterozygotic mutations which, due to the detection of phenotypical properties, such as the enzyme activity derived from the gene product of the reporter gene, are subject to huge fluctuations, which means that in the end no reliable statement is possible. In accordance with the disclosed process, mutations are noticeable only by the absence of positive colonies. In comparison with a wild-type individual, heterozygotically mutated individuals only show a twofold difference in the number of positive colonies whereby statistically-based variations have a considerable adverse effect on the conclusions which can be drawn from the process with regard to the presence of heterozygotic mutations.

SUMMARY OF THE INVENTION

One object of the present invention therefore consists of providing a rapid process for determining mutations in a gene of interest, said process being reliable and easy to carry out. The process is in particular to be suitable for the screening of populations for mutations, whereby a large number of individuals are tested quickly.

The object described above is achieved by a process for detecting mutations in a gene in which the native reading frame is destroyed, by providing a construct which contains a nucleotide sequence which corresponds at least to a section of the coding region of a gene of interest, and a toxin-encoding nucleotide sequence, said construct, downstream from the nucleotide sequence of the gene of interest, being linked to it in its reading frame. After being introduced into a suitable host cell, the construct is expressed in it.

DETAILED DESCRIPTION OF THE PREFERRED EMBODIMENT

Figure 1:
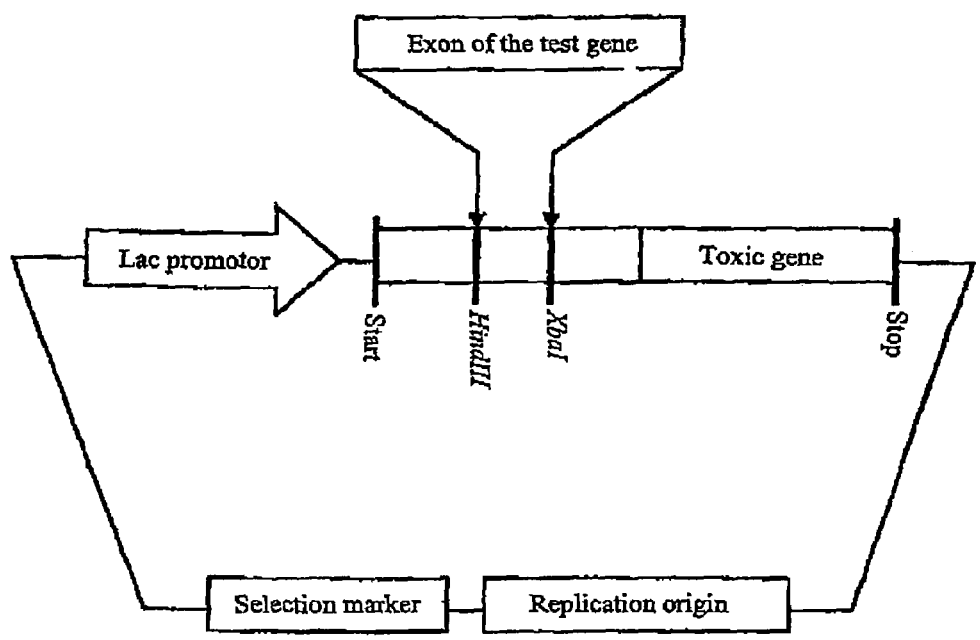
FIG. 1 shows schematically a vector construct for use in the present invention.

In the context of the invention, the native reading frame means the reading frame of a nucleotide sequence which enables a biologically active gene product to be synthesised.

Furthermore, in the present invention, the term "nucleotide sequence which encodes for at least part of a gene of interest" means a nucleotide sequence corresponding to the mRNA of the gene of interest and parts thereof, and also nucleotide sequences derived from the genomic level and containing one or more exonic sequences. Furthermore, it can be derived from genomic DNA from the cell nucleus or from mitochondrial DNA.

A "nucleotide sequence which maintains the reading frame" is a nucleotide sequence approx. 3 to approx. 300 nucleotides long, preferably approx. 30 to approx. 210, more preferably approx. 70 to approx. 210 nucleotides, which is linked in the reading frame to the toxin-encoding nucleotide sequence, and linked in the reading frame to the nucleotide sequence which is encoding for at least part of the gene of interest. In the latter case, the link in the reading frame means the link with the native reading frame.

In the context of the invention, "link in the reading frame" means that a nucleotide sequence is connected to another polypeptide-encoding nucleotide sequence without a stop codon between them so that, at the expression of the construct, a fusion protein can be formed. In the nucleotide sequence which encodes for at least part of a gene of interest, there is therefore no stop codon, which can be achieved by terminating the gene fragment before the native stop codon or by changing the stop codon sequence.

In the implementation of the process, there are now two options.

If the gene to be tested is intact, i.e. it has no mutations introducing a premature stop codon into the gene of interest, possibly due to the point mutation of a nucleotide, or causing a change in the reading frame, such as for example by the insertion or deletion of one or two nucleotides (or multiples thereof, not resulting in a new triplet), then in the expression of the construct, a fusion polypeptide is synthesised which has the amino acid sequence of the gene of interest, or part of it, and at the C terminal the amino acid sequence of the toxin. As the toxin is harmful to the host cell, under these conditions all the cells containing this construct are prevented from growing.

However if the gene to be tested contains one of the aforementioned mutations, then the expression of a polypeptide which is shorter than the fusion polypeptide occurs. Thus, for example, if there is a premature stop codon in the reading frame of the native gene, the synthesised product is shorter than the native product, while if the reading frame is changed, for example by the insertion or deletion of 1, 2, 4 or 5 etc. nucleotides, the new reading frame will continue until there is a stop codon it it. Common to both products is the lack of an active, C-terminal toxin polypeptide in the fusion polypeptide as this was ended either by a stop codon and thus does not have the protein sequence of the toxin or the toxin gene was translated by changing the reading frame in the gene of interest into a protein sequence derived from the toxin gene, said protein sequence not having any toxic effects on the cell.

In this way, if there is a mutation as described, the expression of the construct leads to the growth or to the formation of cell colonies so that it is clear simply by the appearance or growth of cell colonies that the gene of interest has been substantially changed by a mutation.

A process such as this has the advantage over known processes, in particular also over the method disclosed in EP 0 872 560, that the result can be read directly from the growth of the cells. The choice of a toxin, and in particular the "positive selection" of mutants (or negative selection of non-mutants) thus performed, results not only in simplifying the analysis but also has the advantage that heterozygotic mutations can be clearly distinguished from the non-growing cells of wild-type genes.

In this way, a mutation can be detected even in a large excess of wild-type sequences. Furthermore, the growing colonies can be used directly as a source for an amplified gene product for the further characterisation of the mutation, for example by sequencing. This is not possible even with a selection of auxotrophic and prototrophic mutants as the "non-mutated" genes are always selected here.

In accordance with a preferred embodiment, the nucleotide sequence which encodes for at least part of a gene of interest, and the toxin are separated by a nucleotide sequence which maintains the reading frame, and encodes for an amino acid sequence which facilitates the correct folding of the toxin in the presence of the gene product of the gene of interest in the fusion protein.

The present invention is based on the expression and the action of the toxin used in the presence of a native gene sequence. As the gene product of the native gene sequence could negatively affect the folding of the toxin polypeptide due to steric factors, so that it can lose at least part of its toxicity to the host cell, it can be preferable to provide a nucleotide sequence between the nucleotide sequences encoding the gene of interest and the toxin, the said nucleotide sequence encoding amino acids which act as spacers between the two basic bodies of the fusion polypeptides so that the toxin nonetheless folds correctly despite the possible presence of a sterically overflowing gene product of interest and can detect its biological effect. A nucleotide sequence of this kind encodes preferentially for amino acids which themselves do not constitute a steric impediment, such as glycine or alanine for example.

In a further preferred embodiment, a nucleotide sequence which encodes for at least one part of a gene of interest, and which splits the toxin-encoding nucleotide sequence with a nucleotide sequence which maintains the reading frame and in which a stop codon is provided in every reading frame subject to the original reading frame being correct. In this embodiment, the relevant nucleotide sequence contains only one continuous reading frame which is functionally connected to that of the gene of interest and that of the toxin, i.e. in the absence of a mutation resulting in a change to the reading frame in one of the other reading frames, the construct results in a continuous reading frame of three components, the gene of interest, the "intermediate nucleotide sequence" and the toxin. However, if because of a mutation there is a change in the reading frame in the nucleotide sequence which encodes at least part of a gene of interest, then because of the "intermediate nucleotide sequence", the nucleotide sequence of the toxin gene or parts of it cannot be expressed.

The construct containing the various nucleotide sequences listed above also has a promoter and a start codon for the expression of the fusion polypeptide, and suitable sequences for the stable transcription of the construct to the daughter cells and a selection marker. The promoter is preferably inducible. In this way, in an initial embodiment, by adding a substance (inducer) to the culture medium, the promoter can be activated and the polypeptide expressed. If an induction such as this occurs basically immediately after the transformation, only cells containing constructs with mutated nucleotide sequences of interest can grow. However, if the promoter is not activated, all the cells containing a construct will grow. The number of colonies in this case can serve as a control value for the total number of cells containing a construct, regardless of whether from a wild-type or mutated gene.

The toxin can be any gene product suitable or known to be toxic to the corresponding host cell, such as the ccdB gene of F plasmid, the gene E of the phage $\Phi$X174, or colicin for use in bacteria.

Any suitable cell in which the construct can be brought to expression can be used as the host cell for expression of the construct. Examples of suitable host cells are bacteria cells such as E. coli, yeast cells, insect cells or mammal cells, or cell lines derived therefrom. In accordance with a preferred embodiment, E. coli are used as they allow work to be performed quickly and reliably.

The process is highly suitable for screening larger populations, such as animal populations, for example cattle, pigs, goats or sheep. The animals can thus be tested quickly for the presence of a mutation which may be recessive and thus phenotypically not detectable in the particular beasts, but in the event of any interbreeding with another animal also carrying this mutation, can produce offspring in which the mutation has an effect on the phenotype.

The process is also helpful in proving the predisposition of an individual, for example an animal, in particular a human being, to develop a disease.

It is known that tumour suppressor genes play an important role in the occurrence of cancer. They protect the cells against uncontrolled growth. If one allele of the gene is inactivated, there is still a second one which can perform the function. Only a further mutation event in the same gene locus causes the complete switch-off of this important control function. The first mutation can have occurred long before the outbreak of the disease and have remained unknown, or can have been inherited from the parents. The present invention therefore provides a fast and reliable process to determine the predisposition of an individual to develop cancer, by examining tumour suppressor genes in an individual to check their functionality.

The basis of the method is the checking of the open reading frame of the gene in an in vivo test in host cells as previously mentioned (see FIG. 1).

The nucleotide sequence of a gene of interest can be obtained by all known processes, such as by the manufacture of cDNA. The PCR method can also be used, whereby the cDNA thereby produced or an exon, i.e. a continuous piece of the reading frame from genomic DNA of an individual is amplified and then placed in a vector before the toxin. If the reading frame is correct and does not contain stop codons, the toxin is translated and causes the host cell to die.

It is also possible to use several gene fragments in an analysis reaction, regardless of whether they come from the same or different genes. In a preferred embodiment, therefore, a number of gene fragments are amplified simultaneously by multiplex PCR and subsequently analysed for mutations.

With PCR, the primers should have long overhangs for DNA recombination at the 5' end. To ensure, with this arrangement, that yields are not too low and unwanted by-products are not obtained, a so-called two-stage "nested PCR" can be chosen. With this method, an initial PCR stage is carried out with external primers and the product is amplified again selectively in a second stage with internal primers. To enable a rapid sample through-put here, the PCR set-up is carried out in a container without cleaning prior to adding the internal primers. For this, the external primers for the first reaction are selected at a length of approx. 12 to approx. 16 nucleotides, which requires an annealing temperature of around 40° C. To amplify the product using the internal primers, a greater length is chosen for them, i.e. a length and/or nucleotide composition which requires an annealing temperature above the temperature of the first stage (e.g. approx. 50° C.). With this procedure, a desired product can be obtained quickly and highly specifically.

The fragment thus obtained is then inserted in a suitable vector whereby any known process can be used. In accordance with a preferred embodiment, the so-called UDG method is used (see WO 92/22649, the content of which is incorporated herein by reference). Here, PCR primers are used with uracil instead of thymin. The enzyme uracil-DNA-glycosylase (UDG) subsequently cuts out the uracil in the primer area in the PCR products, whereby in this area only the opposite strand in the form of single-strand DNA remains. Incubation at 37° with a similarly treated vector then allows the complementary single-strand DNA areas to accumulate. Following transformation in *E. coli*, the gaps in the DNA are closed by the repair system, whereby functional annular plasmides arise.

After inserting the fragment in a vector, the recombinated DNA molecules are transformed into bacteria cells. Here likewise, any known and suitable transformation method can be used, as described for example in Maniats et al., A Laboratory Handbook (1992).

In accordance with a preferred embodiment, a process is used in which the transformation occurs on a solid culture matrix, such as a culture plate or a membrane. Here, the DNA and the competent bacteria come into contact with each other either only on the matrix or shortly beforehand.

Figure 2:
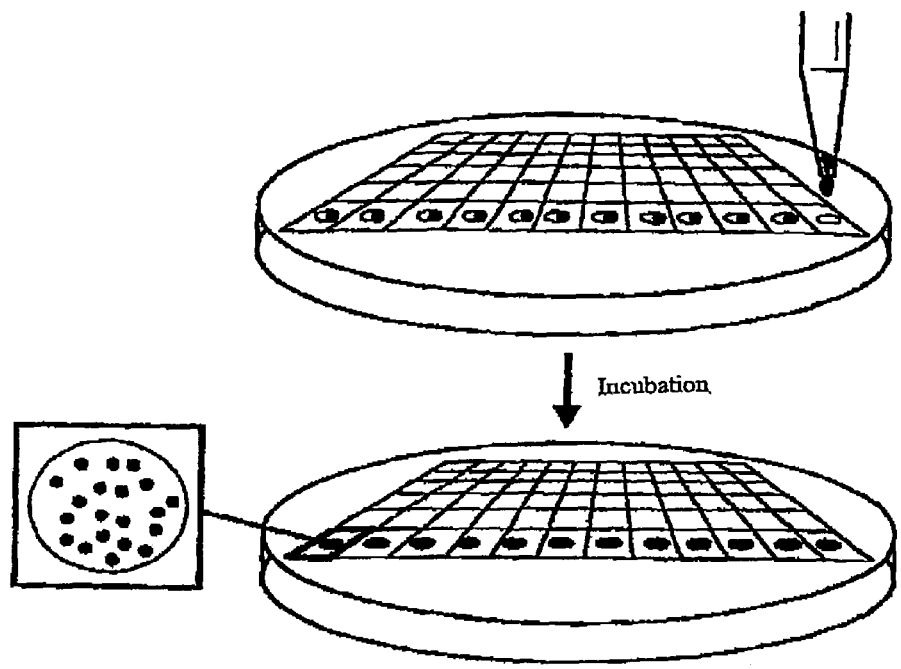
FIG. 2 shows schematically the construct of a plate in the transformation.
Figure 2:
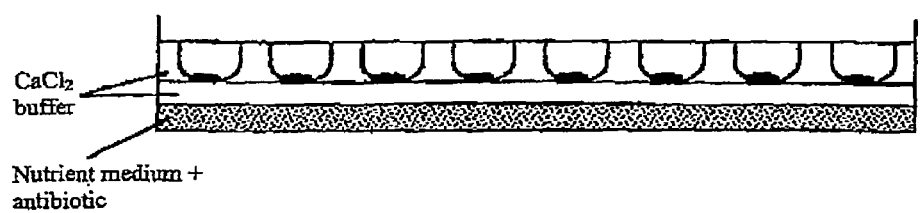
Figure 3:
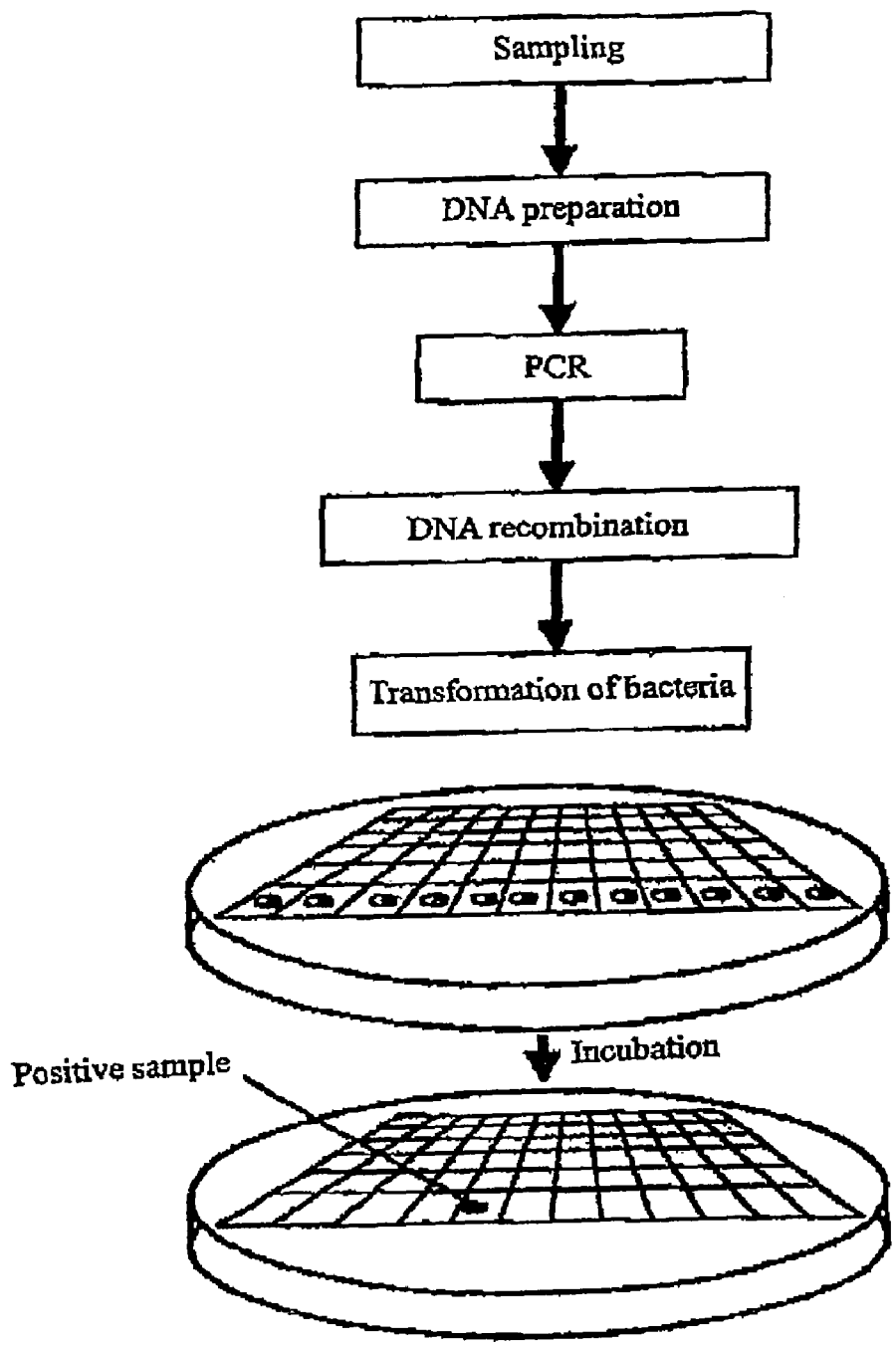
FIG. 3 shows schematically a workflow for identifying a mutation.

The solid culture medium has a multi-layer structure, as shown by way of example in FIG. 2. The uppermost layer holds a buffer containing $CaCl_2$ which competently holds the cells spread on the matrix. The transformation occurs when the nucleic acid to be transformed is brought together with the cells on or in this layer. The layer beneath it contains nutrient medium and possibly a selection marker, such as an antibiotic. During the transformation, therefore, conditions for the uptake of DNA are optimal, following which, if incubation is continued, the nutrients and the selection marker reach the bacteria cells by diffusion and enable them to be cultivated/to multiply.

Where a gel matrix is used, such as an agarose gel, one or more recesses can be made which are a simple way of allowing a number of samples to be processed simultaneously on one plate, e.g. in the standardised 96-well format. Instead of a gel matrix, other substrates can also be used to make the layers. In a preferred embodiment, filter paper is used as the substrate. Once the nutrient medium and the buffer containing $CaCl_2$ have been absorbed, two layers of filter paper are placed over each other and covered with a membrane (made for example of nitrocellulose). DNA and competent bacteria are dripped onto this membrane (either one after the other or after being first incubated together for a short time), whereby after being suitably incubated, bacteria colonies form on the membrane. By using solid substrates such as filter paper, the plate-preparation time can be significantly shortened over that for gel matrices.

The invention is further explained by the following examples which are not however to be regarded as limiting.

EXAMPLE 1

The analysis outline was developed on the pig using the α-1,3-galactosyl transferase gene. The objective is here to identify a pig in which the enzymatic activity of this gene is inactivated, which would be extremely significant for a use with xenotransplantations. The relatively large exon 9 contains around ⅔ of the encoding region of this gene, while the remaining third is split into 4 small exons. However, this large exon is at the end of the encoding region. Nonetheless it is possible to show that even the deletion of the last three amino acids leads to the complete loss of enzymatic activity (Henion et al., Glycobiology 4 (1994), 193). For this reason, this exon was selected for the analysis.

1. Genomic DNA was prepared from tissue samples per the conventional method.

2. Using two-stage PCR, a 729 bp sized fragment of the exon 9 of the α-1,3-galactosyl transferase gene was amplified. In the first stage, the primer pair 1 (oligonucleotides 1 and 2; see Table 1) was used. The reaction occurred in a volume of 20 μl with 10 ng genomic DNA (reaction conditions: 10 mM tris pH 9.2; 50 mM KCl; 1 U taq polymerase; per 0.1 μM primer; 200 μM per dNTP; temperature profile: 5 mins. at 94°, then 15 cycles of 20 s at 94°, 30 s at 38° and 1 min. at 72°). Then 1 µl with 8 pmol each of oligonucleotides 3 and 4 was added and the reaction incubated for a further 20 cycles (temperature profile: 20 s at 94°, 30 s at 54° and 1 min. at 72°, and at the end of the reaction a further incubation of 5 min. at 72°).

3. To make the construct, the plasmide pZERO-2 (IN-VITROGEN/USA), which contains a toxic gene (ccdB) under the control of an inducible lac promoter was adapted. The kanamycin resistance of the plasmide pZERO-2 was however unfavourable for the subsequent transformation and was therefore converted into an ampicillin resistance. To do this, the region of the lac promoter and the ccdB gene was cut out with the help of the restriction enzymes AflIII (LIFE TECHNOLOGIES/Austria) and Eco 147I (FERMENTAS/Germany) and ligated into the plasmide pUC19 (cut with AflIII and AatII (FERMENTAS/Germany) and then treated with T4 DNA polymerase (FERMENTAS/Germany)) (T4 DNA ligase FERMENTAS/Germany, all reactions were carried out in accordance with the company's specifications or standard molecular-biology methods), which resulted in the plasmide pZ. In contrast to the described preparation of the vector for UDG cloning (Rashtchian et al., Analytical Biochemistry 206 (1992), 91)) we established a simplified method which however led to a clear reduction in unwanted by-products. Instead of ligating two complementary oligonucleotides containing uracil at the ends of the cut vector, we used only a phosphorylated oligonucleotide without uracil which was ligated directly into the DNA overhang of the restriction enzyme. In this way, from the outset precisely defined single-strand areas arise at the vector ends. To position the cuts in the reading frame of the polylinker, the plasmide pZ was cut with the enzymes HindIII (LIFE TECHNOLOGIES/Austria) and XbaI (LIFE TECHNOLOGIES/Austria) and ligated with the phosphorylated oligonucleotides 5 and 6, whereby the plasmide pZ2 was obtained. For the DNA recombination, this plasmide was prepared as follows: 5 µg of the plasmide was digested with 40 U each of HindIII (LIFE TECHNOLOGIES/Austria) and XbaI (LIFE TECHNOLOGIES/Austria) as directed by the manufacturer. This was then incubated with 10 U shrimp alkaline phosphatase (FERMENTAS/Germany) for 1 hour at 37° and subsequently the enzyme was inactivated by a 20-minute incubation at 65°. After adding 130 pmol each of phosphorylated oligonucleotides 7 and 8, this was incubated overnight at 14° in a volume of 100 µl with 20 U T4 DNA ligase (FERMENTAS/Germany), 30 U XbaI and ligase buffer according to the manufacturer's instructions. After heating for 10 minutes to 65°, the DNA was cleaned with a 1% agarose gel (with a Cleanmix Kit from TALENT/Italy) and quantified. For the actual recombination reaction, 2 ng of this vector was incubated with 1 µl of the aforesaid PCR reaction, 1 µl of a buffer (10 mM tris pH 8.3; 50 mM KCl; 1.5 mM $MgCl_2$) and 0.1 U uracil DNA glycosylase (LIFE TECHNOLOGIES/Austria) and water in a total volume of 12.5 µl for 90 mins. at 37°.

4. The plates for the transformation were prepared as follows: a first layer of agarose was poured into 15 cm petri dishes (GREINER/Austria), the agarose being made as follows: 25 ml autoclaved LB medium, containing 0.5 g Select Peptone 140 (LIFE TECHNOLOGIES/Austria); 0.25 g yeast extract for bacteriology (ROTH/Germany); 0.25 g NaCl (FLUKA/Austria); 50 µl 1 M NaOH (FLUKA/Austria), was boiled with 0.375 g agarose electrophoresis grade (LIFE TECHNOLOGIES/Austria) and then brought to a temperature of 60°. After adding 10 mg ampicillin (SIGMA/Austria), the plates were poured, after solidification they were dried for 90 minutes under a sterile air current and then kept at 4° for 1 to 3 days. The cooled plates were then kept at 20° for 1 hour and the second agarose layer was then poured, made as follows: 40 ml autoclaved $CaCl_2$ buffer, containing 0.36 g $CaCl_2.H_2O$ (MERCK/Austria) and 0.084 g 3-morpholinopropane sulphonic acid (MERCK/Austria) at a pH of 5.5, was boiled with 0.6 g agarose, then kept at 56°, if necessary 40 µl of a 2 M sterile-filtered IPTG solution (isopropyl-β-D-thiogalactopyranoside, BTS/Germany) was added and then poured onto the first agarose layer. After 10 minutes at room temperature, the plates were dried for 40 mins. in a sterile air current and then cooled on ice for 30 minutes in a cool chamber. A third 35-ml agarose layer was then poured, made in the same way as the second layer, except that after pouring a 96-well format plate with hemispherical recesses was immediately pressed into the agarose layer. After 10 minutes, the plastic form was removed from the solidified agarose layer and the plates incubated again on ice in the cool chamber. After 2 hours, 2 µl of competent bacteria (see below) and 2 µl of the previously described UDG reaction was pipetted into each recess. After a further 30-minute incubation on ice and one hour at room temperature, the plates were incubated uninverted at 37° for approximately 14 hours.

The following protocol was used for the preparation of the competent E. coli bacteria: a single colony of XL10-Gold (STRATEGENE/Germany) was used to inoculate a 50 ml culture with LB medium (see above). After approx. 14 hours incubation in the rocker at 37°, 4 ml was used to inoculate a 400 ml culture (LB medium). At an optical density of 0.3 at 600 nm, the bacteria were incubated on ice for 5 minutes and then centrifuged in a cooling centrifuge (J6-MI BECKMAN/USA; rotor JS-4.2) at 4° at 1600 revolutions for 7 minutes. The excess was removed by suction and the pellet suspended in 10 ml ice-cooled $CaCl_2$ buffer. Per litre, this buffer contains 8.82 g $CaCl_2.H_2O$ (MERCK/Austria), 150 g glycerine water-free high-purity (MERCK/Austria) and 2.1 g 3-morpholinopropane sulphonic acid (MERCK/Austria) at a pH of 7.0 and is autoclaved before use. This solution is centrifuged for 5 minutes at 1,100 revolutions (otherwise as above), the pellet again suspended in 10 ml $CaCl_2$ buffer and incubated on ice for 30 minutes. Following a further centrifugation step (as previously), the pellet is suspended in 2 ml $CaCl_2$ buffer and stored in aliquots at −80°. For the transformation on plates described above, these competent bacteria were diluted 1:9 with ice-cold $CaCl_2$ buffer immediately before the test.

The UDG reaction described above was transformed onto two different plates: one with and one without IPTG (see above). The lac promoter of the vector construct is activated in the presence of IPTG, and consequently the toxic ccdB gene can be expressed. Only on these selective plates, therefore, are mutations detectable by an increased number of colonies. The non-selective plate without IPTG however serves as a control for whether the DNA recombination has functioned at all. As the result, the number of colonies on the selective plate is evaluated as a % of the number of colonies on the non-selective plate. As a positive control, we used a fragment of the exon 9 of the galactosyl transferase which we had mutated in vitro by digestion with the restriction enzymes Bpu1102I and Eco 147I, filling the ends with the Klenow fragment of the DNA polymerase and religation with T4 DNA ligase (all enzymes FERMENTAS/Germany; reaction conditions as specified by the manufacturer). This mutation leads to an 8 bp long deletion which therefore results in a shift of the reading frame. 1 pg of this fragment was used in the PCR instead of genomic DNA. To simulate a heterozygotic situation, we mixed 0.5 pg each of a mutated and a wild-type fragment.

In a typical experiment with DNA samples from 84 pigs, the following results were obtained: 82 samples gave a result of between 0 and 15% colonies on the selective plate with an average of 5.9%, two samples showed less than 5 colonies on the non-selective plate and were therefore not evaluated. The colonies on the selective plate are not due to mutations, but to by-products of the DNA recombination, and taq polymerase errors, as a more precise analysis by means of sequencing showed. 4 positive controls (homozygotic) gave results of 80-105% (mean 97%) and 4 heterozygotic positive controls 41-98% (mean 71%). Unexpectedly, the value for the heterozygotic positive control was well over 50%. In other experiments too we obtained on average values in excess of 50% which is probably due once again to secondary reactions. There is thus sufficient scope to distinguish heterozygotic mutants from wild-type animals. In conclusion, these experiments with galactosyl transferase showed the method to be highly reliable.

EXAMPLE 2

Analysis of Cattle with Stop Codon Mutations

Various mutations of natural origin have previously been described in cattle. Thus, a mutation in the uridine monophosphate synthase gene (DUMPS, deficiency of uridine monophophate synthase) is described as is a mutation which causes citrullinaemia. While these mutations are not wanted, as they cause dangerous metabolism problems in homozygotic individuals, a mutation in the myostatin gene is accompanied by a dramatic increase in muscle mass, which is absolutely a desirable cattle-rearing objective. Common to all these natural mutations is that they lead to the premature destruction of the reading frame. One of these mutations was taken as an example in the uridine monophosphate synthase gene to test this method. The results are shown in Table 1 below:

TABLE 1

|  | Number | % |
|---|---|---|
| wild-type | 1 | ~5 |
|  | 2 | ~5 |
|  | 3 | ~5 |
| heterozygotic | 4 | ~55 |
|  | 5 | ~55 |
|  | 6 | ~55 |

EXAMPLE 3

Analysis of Zebra Fish with Stop Codon Mutations

Due to their short generation time and modest space requirement, some fish species are particularly suitable for genetic experiments. Point mutations in the genome are induced highly efficiently exposure to the mutagenic substance ethylnitrosurea (ENU). In this way, in a number of genetic screens, it was possible to generate hundreds of mutants in zebra fish. In some cases, it was possible to identify the associated genes. One example of this is the bozozok mutant. With the allele bozm168, a premature stop codon is generated by a base exchange whereby the function of the gene is inactivated (Fakany et al., Development 126 (1999), 1427). This allele was used to test the method per the invention taking the example of an induced mutation, whereby the test arrangement per example 1 was used. The results are shown in Table 2 below:

TABLE 2

|  | Number | % |
|---|---|---|
| wild-type | 1 | 9 |
|  | 2 | 10 |
|  | 3 | 10 |
| heterozygotic | 4 | 58 |
|  | 5 | 88 |
|  | 6 | 57 |
| homozygotic | 7 | 75 |
|  | 8 | 100 |
|  | 9 | 116 |

In addition, with these DNA samples the sensitivity of the process was also tested. For this, in a further experiment after the PCR, the fragments were cut from an agarose gel, cleaned (with a Cleanmix Kit from TALENT/Italy) and quantified. The fragments of wild-type DNA were then mixed with small quantities of fragments of heterozygotic mutants. The results are shown in Table 3:

TABLE 3

|  | Number | % |
|---|---|---|
| 100% wild-type | 1 | 2 |
|  | 2 | 1 |
|  | 3 | 2 |
| 80% wild-type + 20% heterozygotic | 4 | 15 |
|  | 5 | 16 |
|  | 6 | 29 |
| 90% wild-type + 10% heterozygotic | 7 | 5 |
|  | 8 | 8 |
|  | 9 | 5.5 |

In this experiment, the cleaned fragments showed a significantly lower number of colonies on the selective plates containing IPTG (average 2%). With a fivefold excess of DNA from heterozygotic fish (corresponding to a tenfold excess of wild-type versus mutated allele), a clear difference from the wild-type samples (average 19%) was to be observed. Even with a further shift in the ratio to a tenfold excess of heterozygotic DNA (corresponding to a twentyfold excess of wild-type versus mutated allele), a small difference in the colony number was still to be observed (average 6%). These experiments show that the process is highly sensitive and can detect mutated alleles even in mixed samples.

What is claimed is:

1. A method for detecting mutations in a gene of interest in which a native reading frame has been destroyed, comprising:
   (a) making a construct comprising a nucleotide sequence which encodes for at least one part of the gene of interest and a toxin-encoding nucleotide sequence which encodes for a toxin and is located downstream from the nucleotide sequence which encodes for at least one part of the gene of interest, and is connected to the latter in its reading frame,
   (b) expressing the construct in a suitable host cell, whereby growth of the host cell is a sign of the mutation in the gene of interest.

2. The method according to claim 1, wherein the nucleotide sequence which encodes for at least one part of the gene of interest, and the toxin-encoding nucleotide sequence are separated by a nucleotide sequence which maintains the reading frame and encodes for an amino acid sequence which supports the correct folding of the toxin in the presence of a gene product of the gene of interest in a fusion protein.

3. The method according to claim 1, wherein the toxin is a ccdB gene of an F plasmid, an E gene of a phage ΦX174 or colicin.

4. The method according to claim 1, wherein the host cell is a bacterial cell, a yeast cell, an insect cell or a mammal cell.

5. A method for screening of an animal population, comprising the method of claim 1.

6. The method according to claim 5, wherein the animal populations are cattle, pigs, goats or sheep.

7. A method for diagnosing a predisposition to develop a disease in an individual, comprising the method of claim 1.

8. The method according to claim 7, wherein the disease is cancer.

9. The method according to claim 8, wherein the gene of interest is a tumor suppressor gene.

10. The method according to claim 5, wherein said animal population is a group of artificially mutated individuals.

* * * * *